United States Patent
Wang et al.

(10) Patent No.: US 12,251,232 B2
(45) Date of Patent: Mar. 18, 2025

(54) MULTI-LABEL ELECTROCARDIOGRAM (ECG) SIGNAL CLASSIFICATION METHOD BASED ON IMPROVED ATTENTION MECHANISM

(71) Applicants: Qilu University of Technology (Shandong Academy of Sciences), Jinan (CN); SHANDONG COMPUTER SCIENCE CENTER (NATIONAL SUPERCOMPUTING CENTER IN JINAN), Jinan (CN)

(72) Inventors: Yinglong Wang, Jinan (CN); Guoxuan Xu, Jinan (CN); Minglei Shu, Jinan (CN); Zhaoyang Liu, Jinan (CN); Pengyao Xu, Jinan (CN)

(73) Assignees: QILU UNIVERSITY OF TECHNOLOGY (SHANDONG ACADEMY OF SCIENCES), Jinan (CN); SHANDONG COMPUTER SCIENCE CENTER (NATIONAL SUPERCOMPUTING CENTER IN JINAN), Jinan (CN)

( * ) Notice: Subject to any disclaimer, the term of this patent is extended or adjusted under 35 U.S.C. 154(b) by 49 days.

(21) Appl. No.: 18/379,182

(22) Filed: Oct. 12, 2023

(65) Prior Publication Data
US 2024/0293070 A1  Sep. 5, 2024

(30) Foreign Application Priority Data
Mar. 3, 2023  (CN) .......................... 202310195187.4

(51) Int. Cl.
*A61B 5/36*  (2021.01)
*A61B 5/00*  (2006.01)
*A61B 5/367*  (2021.01)

(52) U.S. Cl.
CPC ............ *A61B 5/367* (2021.01); *A61B 5/7264* (2013.01)

(58) Field of Classification Search
CPC .............................. A61B 5/7264; A61B 5/367
See application file for complete search history.

(56) References Cited

U.S. PATENT DOCUMENTS 11,678,831 B2 * 6/2023 Fontanarava ........ A61B 5/7275
                                                        600/518
2019/0279361 A1 * 9/2019 Meyer .................. A61B 5/7267
(Continued)

FOREIGN PATENT DOCUMENTS

| CN | 113229825 A | 8/2021 |
| CN | 114190952 A | 3/2022 |
| CN | 115568860 A | 1/2023 |

OTHER PUBLICATIONS

He Kai, et al., Fine-grained image classification algorithm based on multi-scale feature fusion and iterative attention mechanism, Journal of Tianjin University(Science and Technology), 2020, pp. 1077-1085, vol. 53, No. 10.
(Continued)

*Primary Examiner* — Eric D. Bertram
(74) *Attorney, Agent, or Firm* — Bayramoglu Law Offices LLC

(57) ABSTRACT

A multi-label electrocardiogram (ECG) signal classification method based on an improved attention mechanism is provided. A model is constructed for classifying a multi-label (multi-lead) ECG signal. The model has a strong ECG data learning ability, allowing a computer to fully extract a feature of the ECG signal and construct a data processing channel model. Therefore, the multi-label (multi-lead) ECG signal can be effectively classified, improving the accuracy and precision of classification.

6 Claims, 5 Drawing Sheets

(56) References Cited

U.S. PATENT DOCUMENTS

| | | | |
|---|---|---|---|
| 2020/0015755 A1* | 1/2020 | Zhao | A61B 5/7203 |
| 2023/0306267 A1* | 9/2023 | Jacob Banville | G06N 3/0464 |
| 2024/0169198 A1* | 5/2024 | Zubair | G06N 3/082 |
| 2024/0212843 A1* | 6/2024 | Kim | G06N 3/088 |
| 2024/0315632 A1* | 9/2024 | de Bie | A61B 5/361 |
| 2024/0350066 A1* | 10/2024 | Shu | A61B 5/7267 |

OTHER PUBLICATIONS

Shuhong Wang, et al., Multiscale Residual Network Based on Channel Spatial Attention Mechanism for Multilabel ECG Classification, Journal of Healthcare Engineering, 2021, pp. 1-13, vol. 2021, Article ID 6630643.

Xiaoyun Xie, et al., Multilabel 12-Lead ECG Classification Based on Leadwise Grouping Multibranch Network, IEEE Transactions on Instrumentation and Measurement, 2022, vol. 71, 4004111.

* cited by examiner

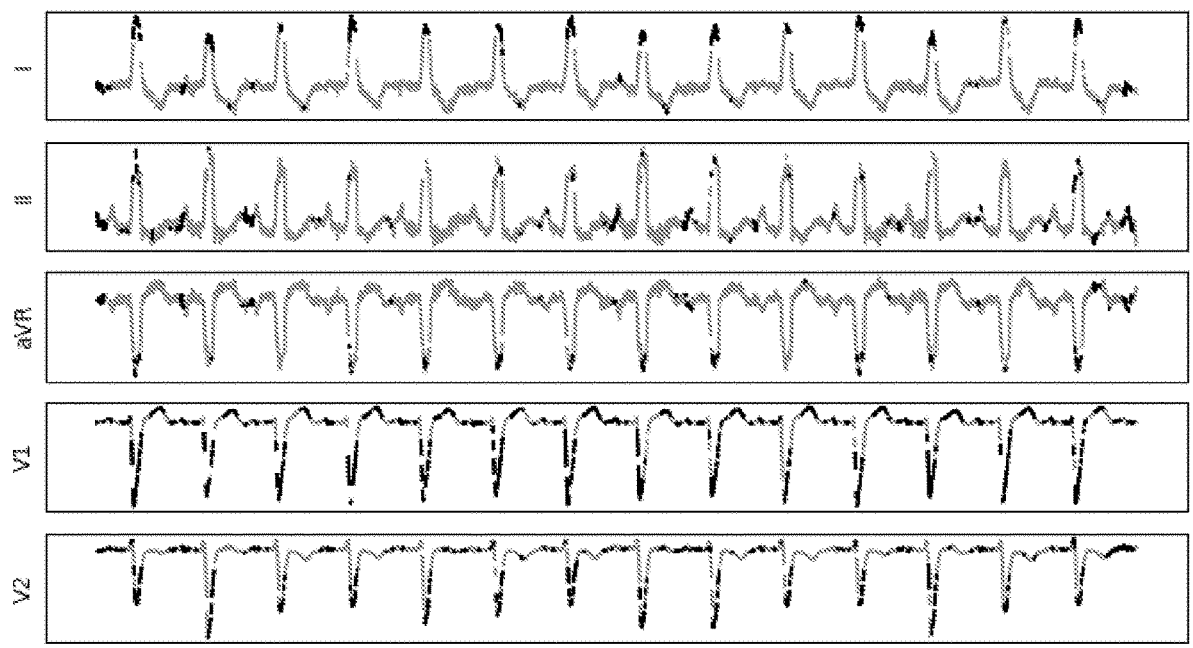
FIG. 2 LBBB type ECG feature visualization effect

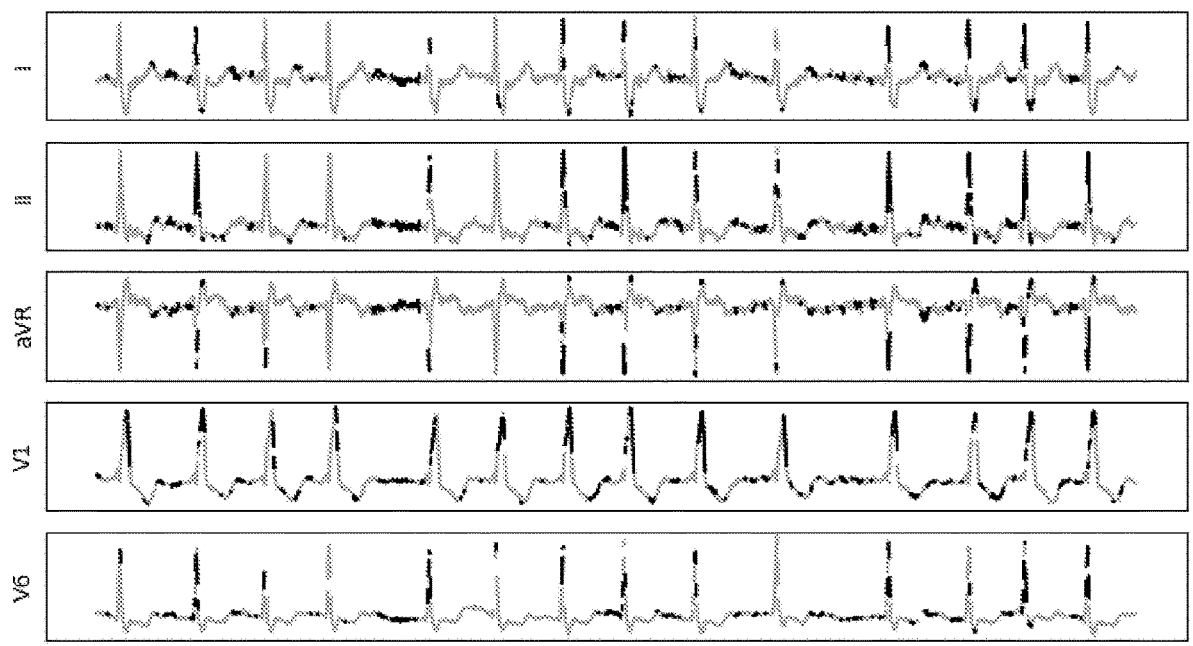
FIG. 3 AF type ECG feature visualization effect

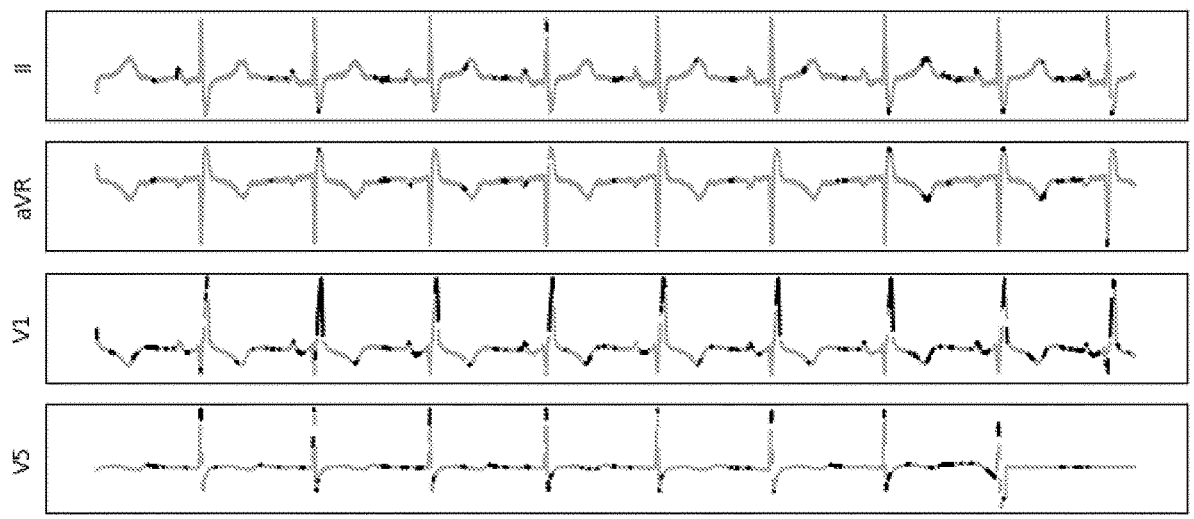
FIG. 4 RBBB type ECG feature visualization effect

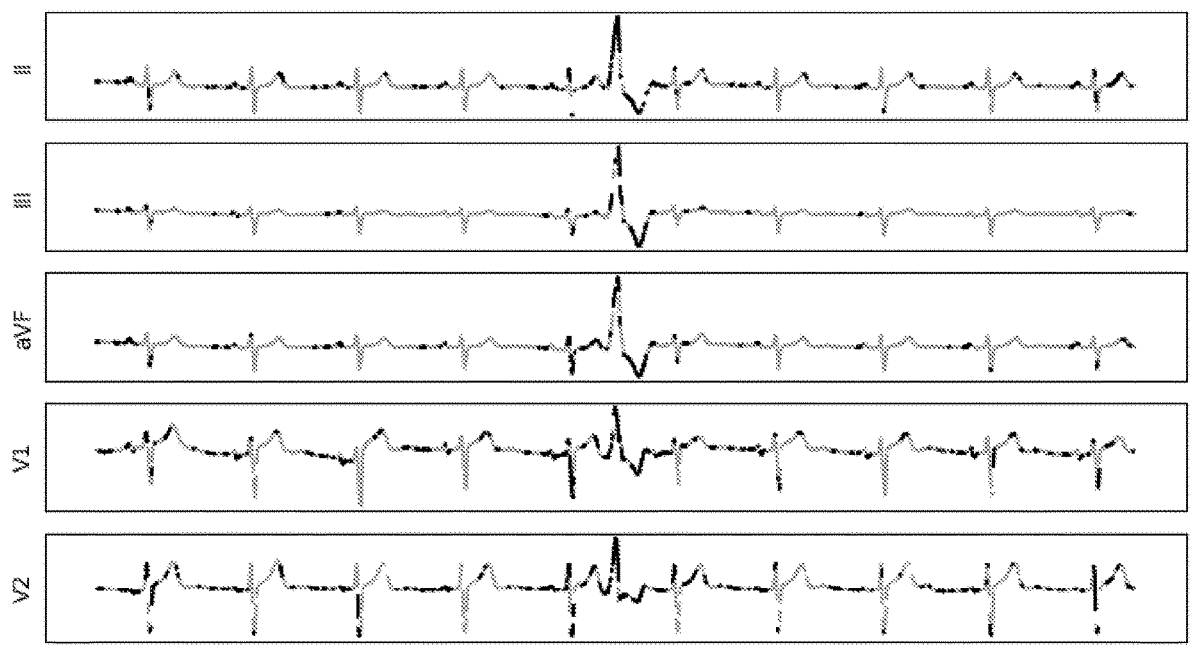
FIG. 5 PVC type ECG feature visualization effect

MULTI-LABEL ELECTROCARDIOGRAM (ECG) SIGNAL CLASSIFICATION METHOD BASED ON IMPROVED ATTENTION MECHANISM

CROSS REFERENCE TO THE RELATED APPLICATIONS

This application is based upon and claims priority to Chinese Patent Application No. 202310195187.4, filed on Mar. 3, 2023, the entire contents of which are incorporated herein by reference.

TECHNICAL FIELD

The present disclosure relates to the technical field of electrocardiogram (ECG) signal classification, and in particular to a multi-label ECG signal classification method based on an improved attention mechanism.

BACKGROUND

Deep learning (DL)-based multi-label ECG signal classification has been widely studied. However, due to the complexity of multi-label ECG signals and insufficient data samples, the accuracy and precision of existing DL models still need to be improved. Specifically, for example, the multi-label ECG signals typically involve multiple leads that have a certain degree of similarity, but the existing models pay less attention to the similarity. Most ECG databases have the problem of imbalanced data samples, which seriously affects the performance of models in recognition and classification. Some multi-label ECG signal classification models based on a self-attention mechanism ignore the similarity between the leads due to a limitation of the self-attention mechanism, and cannot achieve sufficient feature extraction due to the complexity of the signals.

SUMMARY

In order to overcome the above shortcomings of the prior art, the present disclosure provides a method to ensure the integrity of extracting a multi-label electrocardiogram (ECG) signal.

In order to solve the technical problem, the present disclosure adopts the following technical solution.

A multi-label ECG signal classification method based on an improved attention mechanism includes the following steps:
  a) preprocessing a multi-label ECG signal to acquire a preprocessed multi-label ECG signal X;
  b) establishing a multi-scale feature extraction module, and inputting the preprocessed multi-label ECG signal X into the multi-scale feature extraction module to acquire an attention feature map $X_s$;
  c) establishing a deep attention feature fusion (DAFF) network, and inputting the attention feature map $X_s$ into the DAFF network to acquire a fused feature $X'_s$; and
  d) establishing a classification module, and inputting the feature $X'_s$ into the classification module to acquire an ECG signal classification result.

Further, step a) includes the following sub-steps:
  a-1) uniformly adjusting, by downsampling, a data frequency of the multi-label ECG signal to 2,048 sample points to acquire a downsampled multi-label ECG signal; decomposing, by resonance-based sparse decomposition, the downsampled multi-label ECG signal into three parts; and retaining a low-resonance component $x_L$ with an instantaneous oscillation part;
  a-2) cutting all segments in the low-resonance component $x_L$ to a uniform length; and
  a-3) converting, by an unsqueue( ) function or a reshape( ) function, the segments with the uniform length from one-dimensional to two-dimensional, so as to acquire the preprocessed multi-label ECG signal X.

Further, step b) includes the following sub-steps:
  b-1) forming the multi-scale feature extraction module with a residual module A and a residual module B, where the residual module A includes a batch normalization (BN) layer, a rectified linear unit (ReLU) activation function layer, a convolutional layer, a maximum pooling layer, and an attention fusion module; and the residual module B includes a BN layer, a ReLU activation function layer, a convolutional layer, a maximum pooling layer, and an attention fusion module;
  b-2) inputting the preprocessed multi-label ECG signal X into the BN layer, the ReLU activation function layer, and the convolutional layer of the residual module A sequentially to acquire a feature map $X_{sc}^1$;
  b-3) inputting the preprocessed multi-label ECG signal X into the maximum pooling layer of the residual module A to acquire a feature map $X_{sm}^1$;
  b-4) forming the attention fusion module of the residual module A with a local attention block and a global attention block, where the local attention block is formed sequentially with a first convolutional layer, a BN layer, a ReLU activation function layer, and a second convolutional layer; and inputting the feature map $X_{sc}^1$ into the local attention block to acquire a local attention feature map $X_{sc\_l}^1$;
  b-5) forming the global attention block of the attention fusion module in the residual module A sequentially with an average pooling layer, a first convolutional layer, a BN layer, a ReLU activation function layer, and a second convolutional layer; and inputting the feature map $X_{sm}^1$ into the global attention block to acquire a global attention feature map $X_{sc\_g}^1$;
  b-6) adding the local attention feature map $X_{sc\_l}^1$ to the global attention feature map $X_{sc\_g}^1$ to acquire an attention feature map $X_{sa}^1$;
  b-7) inputting the preprocessed multi-label ECG signal X into the BN layer, the ReLU activation function layer, and the convolutional layer of the residual module B sequentially to acquire a feature map $X_{sc}^2$;
  b-8) inputting the preprocessed multi-label ECG signal X into the maximum pooling layer of the residual module B to acquire a feature map $X_{sm}^2$;
  b-9) forming the attention fusion module of the residual module B with a local attention block and a global attention block, where the local attention block is formed sequentially with a first convolutional layer, a BN layer, a ReLU activation function layer, and a second convolutional layer; and inputting the feature map $X_{sc}^2$ into the local attention block to acquire a local attention feature map $X_{sc\_l}^2$;
  b-10) forming the global attention block of the attention fusion module in the residual module B sequentially with an average pooling layer, a first convolutional layer, a BN layer, a ReLU activation function layer, and a second convolutional layer; and inputting the feature map $X_{sm}^2$ into the global attention block to acquire a global attention feature map $X_{sc\_g}^2$;

b-11) adding the local attention feature map $X_{sc\_l}^2$ to the global attention feature map $X_{sc\_g}^2$ to acquire an attention feature map $X_{sa}^2$; and b-12) adding the attention feature map $X_{sa}^1$ to the attention feature map $X_{sa}^2$ to acquire a feature map $X_s$.

Preferably, in step b-1), the convolutional layer of the residual module A is provided with a 1×25 convolution kernel, with a scale of 32; in step b-1), the maximum pooling layer of the residual module A is provided with a 1×2 convolution kernel, with a scale of 32; in step b-4), the first convolutional layer is provided with a 1×1 convolution kernel, with a scale of 16, and the second convolutional layer is provided with a 1×1 convolution kernel, with a scale of 32; in step b-5), the first convolutional layer is provided with a 1×1 convolution kernel, with a scale of 16, and the second convolutional layer is provided with a 1×1 convolution kernel, with a scale of 32; in step b-1), the convolutional layer of the residual module B is provided with a 1×15 convolution kernel, with a scale of 32; in step b-1), the maximum pooling layer of the residual module B is provided with a 1×2 convolution kernel, with a scale of 32; in step b-9), the first convolutional layer is provided with a 1×1 convolution kernel, with a scale of 16, and the second convolutional layer is provided with a 1×1 convolution kernel, with a scale of 32; and in step b-10), the first convolutional layer is provided with a 1×1 convolution kernel, with a scale of 16, and the second convolutional layer is provided with a 1×1 convolution kernel, with a scale of 32.

Further, step c) includes the following sub-steps:

c-1) forming the DAFF network with a first DAFF module and a second DAFF module in parallel, where the first DAFF module and the second DAFF module each include a convolutional layer, a fully connected layer, h parallel self-attention mechanisms, and an attention fusion module;

c-2) inputting the attention feature map $X_s$ into the convolutional layer of the first DAFF module to acquire a feature $X_{sc}^1$; inputting the feature $X_{sc}^1$ into the fully connected layer of the first DAFF module to acquire a new vector $X_s^v$, a new vector $X_s^k$, and a new vector $X_s^q$; inputting the new vector $X_s^v$, the new vector $X_s^k$, and the new vector $X_s^q$ into the h parallel self-attention mechanisms of the first DAFF module to acquire h features $X_{s\_A1}^1, X_{s\_A1}^2, \ldots, X_{s\_A1}^i, \ldots, X_{s\_A1}^h$, where $X_{s\_A1}^i$ denotes a feature output by an i-th self-attention mechanism, $i \in \{1, \ldots, h\}$;

c-3) forming the attention fusion module of the first DAFF module sequentially with a first convolutional layer, a BN layer, a ReLU activation function layer, and a second convolutional layer; inputting the h features $X_{s\_A1}^1, X_{s\_A1}^2, \ldots, X_{s\_A1}^i, \ldots, X_{s\_A1}^h$ into the first convolutional layer to acquire features $X_{s\_A1\_c}^1, X_{s\_A1\_c}^2, \ldots, X_{s\_A1\_c}^i, \ldots, X_{s\_A1\_c}^h$; and inputting the features $X_{s\_A1\_c}^1, X_{s\_A1\_c}^2, \ldots, X_{s\_A1\_c}^i, \ldots, X_{s\_A1\_c}^h$ into the BN layer, the ReLU activation function layer, and the second convolutional layer to acquire new features $X_{s\_A1}^{1'}, X_{s\_A1}^{2'}, \ldots, X_{s\_A1}^{i'}, \ldots, X_{s\_A1}^{h'}$;

c-4) superposing the new features $X_{s\_A1}^{1'}, X_{s\_A1}^{2'}, \ldots, X_{s\_A1}^{i'}, \ldots, X_{s\_A1}^{h'}$ to acquire a feature $X_{s\_A1}$ output by the first DAFF module;

c-5) inputting the attention feature map $X_s$ into the convolutional layer of the second DAFF module to acquire a feature $X_{sc}^2$; inputting the feature $X_{sc}^2$ into the fully connected layer of the second DAFF module to acquire a new vector $X_s^{v'}$, a new vector $X_s^{k'}$, and a new vector $X_s^{q'}$; inputting the new vector $X_s^{v'}$, the new vector $X_s^{k'}$, and the new vector $X_s^{q'}$ into the h parallel self-attention mechanisms of the second DAFF features $X_{s\_B1}^1, X_{s\_B1}^2, \ldots, X_{s\_B1}^i, \ldots, X_{s\_B1}^h$, where $X_{s\_B1}^i$ denotes a feature output by an i-th self-attention mechanism, $i \in \{1, \ldots, h\}$;

c-6) forming the attention fusion module of the second DAFF module sequentially with a first convolutional layer, a BN layer, a ReLU activation function layer, and a second convolutional layer; inputting the h features $X_{s\_B1}^1, X_{s\_B1}^2, \ldots, X_{s\_B1}^i, \ldots, X_{s\_B1}^h$ into the first convolutional layer to acquire features $X_{s\_B1\_c}^1, X_{s\_B1\_c}^2, \ldots, X_{s\_B1\_c}^i, \ldots, X_{s\_B1\_c}^h$; and inputting the features $X_{s\_B1\_c}^1, X_{s\_B1\_c}^2, \ldots, X_{s\_B1\_c}^i, \ldots, X_{s\_B1\_c}^h$ into the BN layer, the ReLU activation function layer, and the second convolutional layer to acquire new features $X_{s\_B1}^{1'}, X_{s\_B1}^{2'}, \ldots, X_{s\_B1}^{i'}, \ldots, X_{s\_B1}^{h'}$;

c-7) superposing the new features $X_{s\_B1}^{1'}, X_{s\_B1}^{2'}, \ldots, X_{s\_B1}^{i'}, \ldots, X_{s\_B1}^{h'}$ to acquire a feature $X_{s\_B1}$ output by the second DAFF module;

c-8) setting a multi-scale feature attention fusion module, where the multi-scale feature attention fusion module sequentially includes an average pooling layer, a first convolutional layer, a BN layer, a ReLU activation function layer, and a second convolutional layer; inputting the feature $X_{s\_A1}$ into the multi-scale feature attention fusion module to acquire a global attention feature map $X'_{s\_A1}$; and inputting the feature $X_{s\_B1}$ into the multi-scale feature attention fusion module to acquire a global attention feature map $X'_{s\_B1}$; and c-9) fusing the global attention feature map $X'_{s\_A1}$ with the global attention feature map $X'_{s\_B1}$ to acquire the feature $X'_s$.

Preferably, in step c-2), the convolutional layer of the first DAFF module is provided with a 3×3 convolution kernel; in step c-3), in the attention fusion module of the first DAFF module, the first convolutional layer is provided with a 1×1 convolution kernel, and the second convolutional layer is provided with a 1×1 convolution kernel; in step c-5), the convolutional layer of the second DAFF module is provided with a 3×3 convolution kernel; in step c-6), in the attention fusion module of the second DAFF module, the first convolutional layer is provided with a 1×1 convolution kernel, and the second convolutional layer is provided with a 1×1 convolution kernel; and in step c-8), the multi-scale feature attention fusion module is provided with a 1×1 average pooling layer, the first convolutional layer is provided with a 1×1 convolution kernel, and the second convolutional layer is provided with a 1×1 convolution kernel.

Further, step d) includes: forming the classification module with a multi-layer perceptron (MLP) and a softmax function, where the MLP sequentially includes a layer normalization (LN) layer and a fully connected layer; inputting the feature $X'_s$ into the MLP; and normalizing, by the softmax function, an output result of the MLP into probabilities of different categories in an interval [0,1].

The present disclosure has the following beneficial effects. The present disclosure provides a multi-label ECG signal classification method based on an improved attention mechanism. The present disclosure constructs a model for classifying a multi-label (multi-lead) ECG signal. The model has a strong ECG data learning ability, allowing a computer to fully extract the feature of the ECG signal and construct a data processing channel model. Therefore, the present disclosure can effectively classify the multi-label (multi-lead) ECG signal, improving the accuracy and precision of classification.

BRIEF DESCRIPTION OF THE DRAWINGS

FIG. 2 shows an LBBB type ECG feature visualization effect;

FIG. 3 shows an AF type ECG feature visualization effect;

FIG. 4 shows an RBBB type ECG feature visualization effect; and

FIG. 5 shows a PVC type ECG feature visualization effect.

DETAILED DESCRIPTION OF THE EMBODIMENTS

Figure 1:
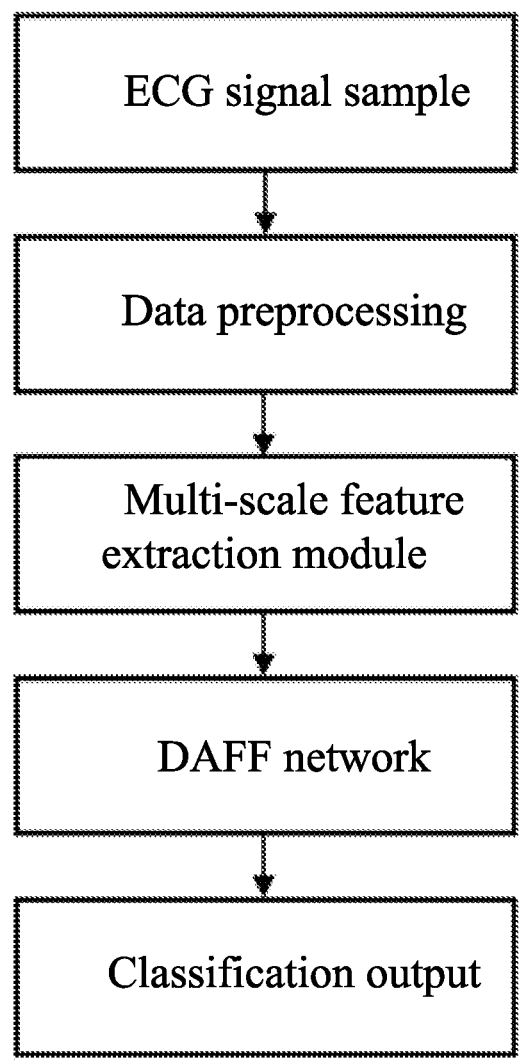
FIG. 1 is a flowchart of a multi-label ECG signal classification method based on an improved attention mechanism according to the present disclosure.

The present disclosure is further described with reference to FIG. 1 and FIG. 2.

A multi-label electrocardiogram (ECG) signal classification method based on an improved attention mechanism includes the following steps.

a) A multi-label ECG signal is preprocessed to acquire preprocessed multi-label ECG signal X.

b) A multi-scale feature extraction module is established, and the preprocessed multi-label ECG signal X is input into the multi-scale feature extraction module to acquire attention feature map $X_s$.

c) A deep attention feature fusion (DAFF) network is established, and the attention feature map $X_s$ is input into the DAFF network to acquire fused feature $X'_s$.

d) A classification module is established, and the feature $X'_s$ is input into the classification module to acquire an ECG signal classification result.

Embodiment 1

Step a) includes the following sub-steps.

a-1) A data frequency of the multi-label ECG signal is uniformly adjusted by downsampling to 2,048 sample points to acquire a downsampled multi-label ECG signal. The downsampled multi-label ECG signal is decomposed by resonance-based sparse decomposition into three parts, and a low-resonance component $x_L$ with an instantaneous oscillation part is retained.

a-2) All segments in the low-resonance component $x_L$ are cut to a uniform length. The segment recorded at a final time is cut without overlap, but segments of other lengths are cut with overlap to meet the conditions and improve data diversity.

a-3) The segments with the uniform length are converted from one-dimensional to two-dimensional by an unsqueue( ) function or a reshape( ) function, so as to acquire the preprocessed multi-label ECG signal X.

Embodiment 2

Step b) includes the following sub-steps.

b-1) The multi-scale feature extraction module is formed with a residual module A and a residual module B, where the residual module A includes a batch normalization (BN) layer, a rectified linear unit (ReLU) activation function layer, a convolutional layer, a maximum pooling layer, and an attention fusion module; and the residual module B includes a BN layer, a ReLU activation function layer, a convolutional layer, a maximum pooling layer, and an attention fusion module.

b-2) The preprocessed multi-label ECG signal X is input into the BN layer, the ReLU activation function layer, and the convolutional layer of the residual module A sequentially to acquire feature map $X_{sc}^1$.

b-3) The preprocessed multi-label ECG signal X is input into the maximum pooling layer of the residual module A to acquire feature map $X_{sm}^1$.

b-4) The attention fusion module of the residual module A is formed with a local attention block and a global attention block, where the local attention block is formed sequentially with a first convolutional layer, a BN layer, a ReLU activation function layer, and a second convolutional layer. The feature map $X_{sc}^1$ is input into the local attention block to acquire local attention feature map $X_{sc\_l}^1$.

b-5) The global attention block of the attention fusion module in the residual module A is formed sequentially with an average pooling layer, a first convolutional layer, a BN layer, a ReLU activation function layer, and a second convolutional layer. The feature map $X_{sm}^1$ is input into the global attention block to acquire global attention feature map $X_{sc\_g}^1$.

b-6) The local attention feature map $X_{sc\_l}^1$ is added to the global attention feature map $X_{sc\_g}^1$ to acquire attention feature map $X_{sa}^1$.

b-7) The preprocessed multi-label ECG signal X is input into the BN layer, the ReLU activation function layer, and the convolutional layer of the residual module B sequentially to acquire feature map $X_{sc}^2$.

b-8) The preprocessed multi-label ECG signal X is input into the maximum pooling layer of the residual module B to acquire feature map $X_{sm}^2$.

b-9) The attention fusion module of the residual module B is formed with a local attention block and a global attention block, where the local attention block is formed sequentially with a first convolutional layer, a BN layer, a ReLU activation function layer, and a second convolutional layer. The feature map $X_{sc}^2$ is input into the local attention block to acquire local attention feature map $X_{sc\_l}^2$.

b-10) The global attention block of the attention fusion module in the residual module B is formed sequentially with an average pooling layer, a first convolutional layer, a BN layer, a ReLU activation function layer, and a second convolutional layer. The feature map $X_{sm}^2$ is input into the global attention block to acquire global attention feature map $X_{sc\_g}^2$.

b-11) The local attention feature map $X_{sc\_l}^2$ is added to the global attention feature map $X_{sc\_g}^2$ to acquire attention feature map $X_{sa}^2$.

b-12) The attention feature map $X_{sa}^1$ is added to the attention feature map $X_{sa}^2$ to acquire feature map $X_s$.

Embodiment 3

In step b-1), the convolutional layer of the residual module A is provided with a 1×25 convolution kernel, with a scale of 32; in step b-1), the maximum pooling layer of the residual module A is provided with a 1×2 convolution kernel, with a scale of 32; in step b-4), the first convolutional layer is provided with a 1×1 convolution kernel, with a scale of 16, and the second convolutional layer is provided with a 1×1 convolution kernel, with a scale of 32; in step b-5), the first convolutional layer is provided with a 1×1 convolution kernel, with a scale of 16, and the second convolutional layer is provided with a 1×1 convolution kernel, with a scale of 32; in step b-1), the convolutional layer of the residual module B is provided with a 1×15 convolution kernel, with a scale of 32; in step b-1), the maximum pooling layer of the residual module B is provided with a 1×2 convolution kernel, with a scale of 32; in step b-9), the first convolutional layer is provided with a 1×1 convolution kernel, with a scale of 16, and the second convolutional layer is provided with a 1×1 convolution kernel, with a scale of 32; and in step b-10), the first convolutional layer is provided with a 1×1 convolution kernel, with a scale of 16, and the second convolutional layer is provided with a 1×1 convolution kernel, with a scale of 32.

Embodiment 4

Step c) includes the following sub-steps.

c-1) The DAFF network is formed with a first DAFF module and a second DAFF module in parallel, where the first DAFF module and the second DAFF module each include a convolutional layer, a fully connected layer, h parallel self-attention mechanisms, and an attention fusion module.

c-2) The attention feature map $X_s$ is input into the convolutional layer of the first DAFF module to acquire feature $X_{sc}^1$ after a dimension reduction process. The feature $X_{sc}^1$ is input into the fully connected layer of the first DAFF module to acquire new vector $X_s^v$, new vector $X_s^k$, and new vector $X_s^q$. The new vector $X_s^v$, the new vector $X_s^k$, and the new vector $X_s^q$ are input into the h parallel self-attention mechanisms of the first DAFF module to acquire h features $X_{s\_A1}^1$, $X_{s\_A1}^2$, ..., $X_{s\_A1}^i$, ..., $X_{s\_A1}^h$, where $X_{s\_A1}^i$ denotes a feature output by an i-th self-attention mechanism, $i \in \{1, ..., h\}$.

c-3) The attention fusion module of the first DAFF module is formed sequentially with a first convolutional layer, a BN layer, a ReLU activation function layer, and a second convolutional layer. The h features $X_{s\_A1}^1$, $X_{s\_A1}^2$, ..., $X_{s\_A1}^i$, ..., $X_{s\_A1}^h$ are input into the first convolutional layer to acquire features $X_{s\_A1\_c}^1$, $X_{s\_A1\_c}^2$, ..., $X_{s\_A1\_c}^i$, ..., $X_{s\_A1\_c}^h$. The features $X_{s\_A1\_c}^1$, $X_{s\_A1\_c}^2$, ..., $X_{s\_A1\_c}^i$, ..., $X_{s\_A1\_c}^h$ are input into the BN layer, the ReLU activation function layer, and the second convolutional layer to acquire new features $X_{s\_A1}^{1'}$, $X_{s\_A1}^{2'}$, ..., $X_{s\_A1}^{i'}$, ..., $X_{s\_A1}^{h'}$.

c-4) The new features $X_{s\_A1}^{1'}$, $X_{s\_A1}^{2'}$, ..., $X_{s\_A1}^{i'}$, ..., $X_{s\_A1}^{h'}$ are superposed to acquire feature $X_{s\_A1}$ output by the first DAFF module.

c-5) The attention feature map $X_s$ is input into the convolutional layer of the second DAFF module to acquire feature $X_{sc}^2$ after a dimension reduction process. The feature $X_{sc}^2$ is input into the fully connected layer of the second DAFF module to acquire new vector $X_s^{v'}$, new vector $X_s^{k'}$, and new vector $X_s^{q'}$. The new vector $X_s^{v'}$, the new vector $X_s^{k'}$, and the new vector $X_s^{q'}$ are input into the h parallel self-attention mechanisms of the second DAFF module to acquire h features $X_{s\_B1}^1$, $X_{s\_B1}^2$, ..., $X_{s\_B1}^i$, ..., $X_{s\_B1}^h$, where $X_{s\_B1}^i$ denotes a feature output by an i-th self-attention mechanism, $i \in \{1, ..., h\}$.

c-6) The attention fusion module of the second DAFF module is formed sequentially with a first convolutional layer, a BN layer, a ReLU activation function layer, and a second convolutional layer. The h features $X_{s\_B1}^1$, $X_{s\_B1}^2$, ..., $X_{s\_B1}^i$, ..., $X_{s\_B1}^h$ are input into the first convolutional layer to acquire features $X_{s\_B1\_c}^1$, $X_{s\_B1\_c}^2$, ..., $X_{s\_B1\_c}^i$, ..., $X_{s\_B1\_c}^h$. The features $X_{s\_B1\_c}^1$, $X_{s\_B1\_c}^2$, ..., $X_{s\_B1\_c}^i$, ..., $X_{s\_B1\_c}^h$ are input into the BN layer, the ReLU activation function layer, and the second convolutional layer to acquire new features $X_{s\_B1}^{1'}$, $X_{s\_B1}^{2'}$, ..., $X_{s\_B1}^{i'}$, ..., $X_{s\_B1}^{h'}$.

c-7) The new features $X_{s\_B1}^{1'}$, $X_{s\_B1}^{2'}$, ..., $X_{s\_B1}^{i'}$, ..., $X_{s\_B1}^{h'}$ are superposed to acquire feature $X_{s\_B1}$ output by the second DAFF module.

c-8) A multi-scale feature attention fusion module is set, where the multi-scale feature attention fusion module sequentially includes an average pooling layer, a first convolutional layer, a BN layer, a ReLU activation function layer, and a second convolutional layer. The feature $X_{s\_A1}$ is input into the multi-scale feature attention fusion module to acquire global attention feature may $X'_{s\_A1}$. The feature $X_{s\_B1}$ is input into the multi-scale feature attention feature attention fusion module to acquire global attention feature map $X'_{s\_B1}$.

c-9) The global attention feature map $X'_{s\_A1}$ is fused with the global attention feature map $X'_{s\_B1}$ to acquire the feature $X'_s$.

Embodiment 5

In step c-2), the convolutional layer of the first DAFF module is provided with a 3×3 convolution kernel; in step c-3), in the attention fusion module of the first DAFF module, the first convolutional layer is provided with a 1×1 convolution kernel, and the second convolutional layer is provided with a 1×1 convolution kernel; in step c-5), the convolutional layer of the second DAFF module is provided with a 3×3 convolution kernel; in step c-6), in the attention fusion module of the second DAFF module, the first convolutional layer is provided with a 1×1 convolution kernel, and the second convolutional layer is provided with a 1×1 convolution kernel; and in step c-8), the multi-scale feature attention fusion module is provided with a 1×1 average pooling layer, the first convolutional layer is provided with a 1×1 convolution kernel, and the second convolutional layer is provided with a 1×1 convolution kernel.

Embodiment 6

In step d), the classification module is formed with a multi-layer perceptron (MLP) and a softmax function, where the MLP sequentially includes a layer normalization (LN) layer and a fully connected layer. The feature $X'_s$ is input into the MLP. An output result of the MLP is normalized by the softmax function into probabilities of different categories in an interval [0,1]. The probability refers to a final ECG signal classification result.

The following is an example to illustrate the implementation of the method of the present disclosure through publicly available dataset PTb-XL.

ECG signal data and corresponding ECG anomaly type labels are acquired from the dataset PTb-XL, and a multi-label ECG signal classification model is established based on an improved attention mechanism. This model includes a data preprocessing module, a multi-scale feature extraction module, a DAFF network, and an output module. The ECG data from the dataset PTb-XL are preprocessed, and down-sampled to acquire 2,048 sample points of the ECG data. The one-dimensional ECG signal is converted into a two-dimensional data by an unsqueeeze( ) function to acquire preprocessed ECG signal X.

In the multi-label ECG signal classification model based on the improved attention mechanism, the preprocessed ECG signal X is input into the multi-scale feature module formed by residual module A and residual module B in parallel. The feature X is processed by the residual module A to acquire attention feature map $X_{sa}^1$, and the feature X is processed by the residual module B to acquire attention feature map $X_{sa}^2$. The attention feature map $X_{sa}^1$ is added to the attention feature map $X_{sa}^2$ to acquire feature map $X_s$ output by the sa multi-scale feature module. The feature map $X_s$ is input into the DAFF network including a first DAFF module and a second DAFF module in parallel. The feature $X_s$ is processed by the first DAFF module to acquire new feature map $X_{s\_A1}$, and the feature $X_s$ is processed by the second DAFF module to acquire new feature map $X_{s\_B1}$. The new feature $X_{s\_A1}$ and the feature $X_{s\_B1}$ are processed by the multi-scale feature attention fusion module to acquire feature $X'_{s\_A1}$ and feature $X'_{s\_B1}$. The feature $X'_{s\_A1}$ and the new feature $X'_{s\_B1}$ are fused to acquire feature $X'_s$. The feature is input into the classification module to acquire a final classification result.

The model of the present disclosure is compared with classical neural network models (LSTM, Xresnet) and state-of-the-art neural network temporal models (InceptionTime, ECG-Net, SE-ECGNet, and ACNet). Comparative experiments are conducted under unified conditions to demonstrate the effectiveness of the method of the present disclosure. As shown in Table 1, two metrics, namely macro-area under the curve (AUC) and F1-score. F1-score is the weighted average of accuracy and recall.

The training is conducted based on the dataset PTb-XL, and the relevant metrics of the model are evaluated. The experimental results are shown in Table 1. For the sake of fairness, all models compared are tested under unified conditions. Six classification tasks in the dataset PTb-XL are tested, and the model of the present disclosure performs better than the other six models in two mainstream metrics. In the 71 label classification tasks (ALL), the model of the present disclosure performs 0.83% better in the macro-AUC metric than the state-of-the-art ECG classification models, and the F1-score acquired by the model of the present disclosure is 1.15% higher than the state-of-the-art models, proving that the method of the present disclosure has excellent classification detection ability. In the other five classification tasks, the model of the present disclosure has varying degrees of leading performance. This indicates that the network of the present disclosure has better classification performance when processing complex data compared to other state-of-the-art networks. Meanwhile, this also indicates that the network of the present disclosure has high performance in detecting real diseases.

Table 2 shows the comparison result of the F1-score between the method of the present disclosure and the nine related models on dataset CPSC-2018. Compared with the general temporal classification model Inception-Time, the method of the present disclosure improves the average F1-score by 2.71%. Compared with another attention module based SE-ECG Net, the method of the present disclosure improves the average F1-score by 2.26%, with almost the highest increase in the F1-score in atrial fibrillation (AF), first-degree atrioventricular block (I-AVB), and left bundle branch block (LBBB). This fully demonstrates the enormous potential of the model of the present disclosure in mining fine-grained features of ECG signals. In summary, the model of the present disclosure has higher accuracy in detecting most ECG abnormalities and is more competitive than other state-of-the-art methods.

The corresponding features are visualized in the ECG through Shapley Additive exPlanations (shaps). FIG. 2 shows a visualization result of LBBB predicted by the model of the present disclosure, where the deep S-wave in lead V1 is consistent with the landmark feature of the identified LBBB. FIG. 3 shows a recognition effect of the model of the present disclosure on irregular QRS waves. A typical example of AF is the lack of P-waves. The result shown in FIG. 3 is consistent with the criterion for determining the AF. FIG. 4 shows a feature visualization result of right bundle branch block (RBBB), which is acquired by detecting the QRS waves in the V1 lead. FIG. 5 shows a feature visualization result of premature ventricular contraction (PVC), where PVC only occurs during a scattered period in the ECG.

TABLE 1

Comparison results of models on dataset PTB-XL

| Network | ALL | | Diag | | Sub-diag. | | Super-diag. | | Form | | Rhythm | |
|---|---|---|---|---|---|---|---|---|---|---|---|---|
| | AUC | F1-score | AUC | F1-score | AUC | F1-score | AUC | F1-score | AUC | F1-score | AUC | F1-score |
| Inception Time | 91.42 | 71.95 | 93.61 | 65.98 | 93.41 | 68.9 | 91.0 | 76.6 | 88.51 | 53.02 | 93.41 | 90.15 |
| Xresnet | 91.73 | 70.67 | 92 | 64.65 | 91.26 | 66.84 | 91.09 | 73.5 | 84.02 | 50.56 | 95.04 | 90.91 |
| ECG-Net | 91.74 | 70.13 | 91.14 | 66.01 | 91.17 | 68.94 | 92.28 | 76.23 | 87.67 | 52.16 | 96.16 | 91.69 |
| LSTM | 89.8 | 70.95 | 91.29 | 65.87 | 91.39 | 68.37 | 92.04 | 77.32 | 85.04 | 53.38 | 96.57 | 91.75 |
| ACNet | 87.58 | 67.77 | 87.63 | 61.73 | 87.5 | 63.94 | 91.71 | 76.42 | 81.14 | 46.49 | 95.91 | 92.45 |
| SE-ECGNet | 87.26 | 68.18 | 85.8 | 59.88 | 87.11 | 63.1 | 88.43 | 70.19 | 78.62 | 40.98 | 94.55 | 89.47 |
| Ours | 92.57 | 73.1 | 94.12 | 68.57 | 93.53 | 69.74 | 92.76 | 77.28 | 88.74 | 53.66 | 96.65 | 92.58 |

TABLE 2

Comparison results of models on dataset CPSC-2018

| Method | Inception Time | IMLE | ECG-Net | ATI-CNN | ACNet | Xresnet01 | Fcnwang | LSTM | SE-ECGNet | Ours |
|---|---|---|---|---|---|---|---|---|---|---|
| Normal | 78.67 | 78.92 | 77.58 | 75.73 | 77.83 | 78.57 | 74.62 | 73.41 | 78.73 | 79.12 |
| AF | 84.97 | 87.91 | 85.36 | 84.92 | 85.27 | 88.36 | 84.74 | 83.59 | 86.41 | 91.36 |
| RBBB | 86.41 | 88.73 | 84.95 | 87.35 | 90.31 | 88.71 | 86.31 | 84.27 | 89.52 | 90.64 |
| I-AVB | 83.29 | 87.45 | 86.61 | 83.62 | 84.97 | 84.90 | 85.06 | 81.62 | 82.17 | 88.88 |
| STD | 77.8 | 77.91 | 75.29 | 76.58 | 74.82 | 76.58 | 74.18 | 73.89 | 76.81 | 78.21 |

TABLE 2-continued

Comparison results of models on dataset CPSC-2018

| Method | Inception Time | IMLE | ECG-Net | ATI-CNN | ACNet | Xresnet01 | Fcnwang | LSTM | SE-ECGNet | Ours |
|---|---|---|---|---|---|---|---|---|---|---|
| PAC | 74.93 | 75.63 | 73.82 | 75.24 | 73.61 | 74.25 | 73.40 | 72.70 | 75.53 | 75.71 |
| PVC | 87.1 | 85.41 | 83.53 | 82.73 | 81.43 | 85.94 | 83.72 | 84.58 | 86.32 | 86.70 |
| LBBB | 84.31 | 87.8 | 85.74 | 82.49 | 85.63 | 86.17 | 84.25 | 85.46 | 84.79 | 88.52 |
| STE | 67.1 | 69.56 | 66.15 | 68.06 | 67.82 | 67.40 | 66.83 | 65.73 | 68.27 | 69.77 |
| Average | 80.50 | 82.14 | 79.89 | 79.63 | 80.18 | 81.21 | 79.23 | 78.36 | 80.95 | 83.21 |

What is claimed is:

1. A multi-label electrocardiogram (ECG) signal classification method based on an improved attention mechanism, comprising the following steps:
   a) preprocessing a multi-label ECG signal to acquire a preprocessed multi-label ECG signal X;
   b) establishing a multi-scale feature extraction module, and inputting the preprocessed multi-label ECG signal X into the multi-scale feature extraction module to acquire an attention feature map $X_s$;
   c) establishing a deep attention feature fusion (DAFF) network, and inputting the attention feature map $X_s$ into the DAFF network to acquire a fused feature $X'_s$; and
   d) establishing a classification module, and inputting the feature $X'_s$ into the classification module to acquire an ECG signal classification result;
   wherein step b) comprises the following sub-steps:
   b-1) forming the multi-scale feature extraction module with a residual module A and a residual module B, wherein the residual module A comprises a batch normalization (BN) layer, a rectified linear unit (ReLU) activation function layer, a convolutional layer, a maximum pooling layer, and an attention fusion module; and the residual module B comprises a BN layer, a ReLU activation function layer, a convolutional layer, a maximum pooling layer, and an attention fusion module;
   b-2) inputting the preprocessed multi-label ECG signal X into the BN layer, the ReLU activation function layer, and the convolutional layer of the residual module A sequentially to acquire a feature map $X_{sc}^1$;
   b-3) inputting the preprocessed multi-label ECG signal X into the maximum pooling layer of the residual module A to acquire a feature map $X_{sm}^1$;
   b-4) forming the attention fusion module of the residual module A with a local attention block and a global attention block, wherein the local attention block is formed sequentially with a first convolutional layer, a BN layer, a ReLU activation function layer, and a second convolutional layer; and inputting the feature map $X_{sc}^1$ into the local attention block to acquire a local attention feature map $X_{sc\_l}^1$;
   b-5) forming the global attention block of the attention fusion module in the residual module A sequentially with an average pooling layer, a first convolutional layer, a BN layer, a ReLU activation function layer, and a second convolutional layer; and inputting the feature map $X_{sm}^1$ into the global attention block to acquire a global attention feature map $X_{sc\_g}^1$;
   b-6) adding the local attention feature map $X_{sc\_l}^1$ to the global attention feature map $X_{sc\_g}^1$ to acquire an attention feature map $X_{sa}^1$;
   b-7) inputting the preprocessed multi-label ECG signal X into the BN layer, the ReLU activation function layer, and the convolutional layer of the residual module B sequentially to acquire a feature map $X_{sc}^2$;
   b-8) inputting the preprocessed multi-label ECG signal X into the maximum pooling layer of the residual module B to acquire a feature map $X_{sm}^2$;
   b-9) forming the attention fusion module of the residual module B with a local attention block and a global attention block, wherein the local attention block is formed sequentially with a first convolutional layer, a BN layer, a ReLU activation function layer, and a second convolutional layer; and inputting the feature map $X_{sc}^2$ into the local attention block to acquire a local attention feature map $X_{sc\_l}^2$;
   b-10) forming the global attention block of the attention fusion module in the residual module B sequentially with an average pooling layer, a first convolutional layer, a BN layer, a ReLU activation function layer, and a second convolutional layer; and inputting the feature map $X_{sm}^2$ into the global attention block to acquire a global attention feature map $X_{sc\_g}^2$;
   b-11) adding the local attention feature map $X_{sc\_l}^1$ to the global attention feature map $X_{sc\_g}^2$ to acquire an attention feature map $X_{sa}^2$; and
   b-12) adding the attention feature map $X_{sa}^1$ to the attention feature map $X_{sa}^2$ to acquire a feature map $X_s$.

2. The multi-label ECG signal classification method based on the improved attention mechanism according to claim 1, wherein step a) comprises the following sub-steps:
   a-1) uniformly adjusting, by downsampling, a data frequency of the multi-label ECG signal to 2,048 sample points to acquire a downsampled multi-label ECG signal; decomposing, by resonance-based sparse decomposition, the downsampled multi-label ECG signal into three parts; and retaining a low-resonance component $x_L$ with an instantaneous oscillation part;
   a-2) cutting all segments in the low-resonance component $x_L$ to a uniform length; and
   a-3) converting, by an unsqueue( ) function or a reshape( ) function, the segments with the uniform length from one-dimensional to two-dimensional to acquire the preprocessed multi-label ECG signal X.

3. The multi-label ECG signal classification method based on the improved attention mechanism according to claim 1, wherein
   in step b-1), the convolutional layer of the residual module A is provided with a 1×25 convolution kernel, with a scale of 32;
   in step b-1), the maximum pooling layer of the residual module A is provided with a 1×2 convolution kernel, with a scale of 32;
   in step b-4), the first convolutional layer is provided with a 1×1 convolution kernel, with a scale of 16, and the second convolutional layer is provided with a 1×1 convolution kernel, with a scale of 32;

in step b-5), the first convolutional layer is provided with a 1×1 convolution kernel, with a scale of 16, and the second convolutional layer is provided with a 1×1 convolution kernel, with a scale of 32;

in step b-1), the convolutional layer of the residual module B is provided with a 1×15 convolution kernel, with a scale of 32;

in step b-1), the maximum pooling layer of the residual module B is provided with a 1×2 convolution kernel, with a scale of 32;

in step b-9), the first convolutional layer is provided with a 1×1 convolution kernel, with a scale of 16, and the second convolutional layer is provided with a 1×1 convolution kernel, with a scale of 32; and in step b-10), the first convolutional layer is provided with a 1×1 convolution kernel, with a scale of 16, and the second convolutional layer is provided with a 1×1 convolution kernel, with a scale of 32.

4. The multi-label ECG signal classification method based on the improved attention mechanism according to claim 1, wherein step c) comprises the following sub-steps:

c-1) forming the DAFF network with a first DAFF module and a second DAFF module in parallel, wherein the first DAFF module and the second DAFF module each comprise a convolutional layer, a fully connected layer, h parallel self-attention mechanisms, and an attention fusion module;

c-2) inputting the attention feature map $X_s$ into the convolutional layer of the first DAFF module to acquire a feature $X_{sc}^1$; inputting the feature $X_{sc}^1$ into the fully connected layer of the first DAFF module to acquire a new vector $X_s^v$, a new vector $X_s^k$, and a new vector $X_s^q$; inputting the new vector $X_s^v$, the new vector $X_s^k$, and the new vector $X_s^q$ into the h parallel self-attention mechanisms of the first DAFF module to acquire h features $X_{s\_A1}^1, X_{s\_A1}^2, \ldots, X_{s\_A1}^i, \ldots, X_{s\_A1}^h$, wherein $X_{s\_A1}^i$ denotes a feature output by an i-th self-attention mechanism, $i \in \{1, \ldots, h\}$;

c-3) forming the attention fusion module of the first DAFF module sequentially with a first convolutional layer, a BN layer, a ReLU activation function layer, and a second convolutional layer; inputting the h features $X_{s\_A1}^1, X_{s\_A1}^2, \ldots, X_{s\_A1}^i, \ldots, X_{s\_A1}^h$ into the first convolutional layer to acquire features $X_{s\_A1\_c}^1, X_{s\_A1\_c}^2, \ldots, X_{s\_A1\_c}^i, \ldots, X_{s\_A1\_c}^h$; and inputting the features $X_{s\_A1\_c}^1, X_{s\_A1\_c}^2, \ldots, X_{s\_A1\_c}^i, \ldots, X_{s\_A1\_c}^h$ into the BN layer, the ReLU activation function layer, and the second convolutional layer to acquire new features $X_{s\_A1}^{1'}, X_{s\_A1}^{2'}, \ldots, X_{s\_A1}^{i'}, \ldots, X_{s\_A1}^{h'}$;

c-4) superposing the new features $X_{s\_A1}^{1'}, X_{s\_A1}^{2'}, \ldots, X_{s\_A1}^{i'}, \ldots, X_{s\_A1}^{h'}$ to acquire a feature $X_{s\_A1}$ output by the first DAFF module;

c-5) inputting the attention feature map $X_s$ into the convolutional layer of the second DAFF module to acquire a feature $X_{sc}^2$; inputting the feature $X_{sc}^2$ into the fully connected layer of the second DAFF module to acquire a new vector $X_s^{v'}$, a new vector $X_s^{k'}$, and a new vector $X_s^{q'}$; inputting the new vector $X_s^{v'}$, the new vector $X_s^{k'}$, and the new vector $X_s^{q'}$ into the h parallel self-attention mechanisms of the second DAFF module to acquire h features $X_{s\_B1}^1, X_{s\_B1}^2, \ldots, X_{s\_B1}^i, \ldots, X_{s\_B1}^h$; wherein $X_{s\_B1}^i$ denotes a feature output by an i-th self-attention mechanism, $i \in \{1, \ldots, h\}$;

c-6) forming the attention fusion module of the second DAFF module sequentially with a first convolutional layer, a BN layer, a ReLU activation function layer, and a second convolutional layer; inputting the h features $X_{s\_B1}^1, X_{s\_B1}^2, \ldots, X_{s\_B1}^i, \ldots, X_{s\_B1}^h$ into the first convolutional layer to acquire features $X_{s\_B1\_c}^1, X_{s\_B1\_c}^2, \ldots, X_{s\_B1\_c}^i, \ldots, X_{s\_B1\_c}^h$; and inputting the features $X_{s\_B1\_c}^1, X_{s\_B1\_c}^2, \ldots, X_{s\_B1\_c}^i, \ldots, X_{s\_B1\_c}^h$ into the BN layer, the ReLU activation function layer, and the second convolutional layer to acquire new features $X_{s\_B1}^{1'}, X_{s\_B1}^{2'}, \ldots, X_{s\_B1}^{i'}, \ldots, X_{s\_B1}^{h'}$;

c-7) superposing the new features $X_{s\_B1}^{1'}, X_{s\_B1}^{2'}, \ldots, X_{s\_B1}^{i'}, \ldots, X_{s\_B1}^{h'}$ to acquire a feature $X_{s\_B1}$ output by the second DAFF module;

c-8) setting a multi-scale feature attention fusion module, wherein the multi-scale feature attention fusion module sequentially comprises an average pooling layer, a first convolutional layer, a BN layer, a ReLU activation function layer, and a second convolutional layer; inputting the feature $X_{s\_A1}$ into the multi-scale feature attention fusion module to acquire a global attention feature map $X'_{s\_A1}$; and inputting the feature $X_{s\_B1}$ into the multi-scale feature attention fusion module to acquire a global attention feature map $X'_{s\_B1}$; and c-9) fusing the global attention feature map $X'_{s\_A1}$ with the global attention feature map $X'_{s\_B1}$ to acquire the feature $X'_s$.

5. The multi-label ECG signal classification method based on the improved attention mechanism according to claim 4, wherein in step c-2), the convolutional layer of the first DAFF module is provided with a 3×3 convolution kernel;

in step c-3), in the attention fusion module of the first DAFF module, the first convolutional layer is provided with a 1×1 convolution kernel, and the second convolutional layer is provided with a 1×1 convolution kernel;

in step c-5), the convolutional layer of the second DAFF module is provided with a 3×3 convolution kernel;

in step c-6), in the attention fusion module of the second DAFF module, the first convolutional layer is provided with a 1×1 convolution kernel, and the second convolutional layer is provided with a 1×1 convolution kernel; and in step c-8), the multi-scale feature attention fusion module is provided with a 1×1 average pooling layer, the first convolutional layer is provided with a 1×1 convolution kernel, and the second convolutional layer is provided with a 1×1 convolution kernel.

6. The multi-label ECG signal classification method based on the improved attention mechanism according to claim 1, wherein step d) comprises: forming the classification module with a multi-layer perceptron (MLP) and a softmax function, wherein the MLP sequentially comprises a layer normalization (LN) layer and a fully connected layer; inputting the feature $X'_s$ into the MLP; and normalizing, by the softmax function, an output result of the MLP into probabilities of different categories in an interval [0,1].

* * * * *